(12) United States Patent
Hestad et al.

(10) Patent No.: US 7,371,213 B2
(45) Date of Patent: May 13, 2008

(54) LIT RETRACTOR

(75) Inventors: Hugh D. Hestad, Edina, MN (US);
Dean M J Acker, Warsaw, IN (US);
Robert D. Krebs, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 449 days.

(21) Appl. No.: 11/072,376

(22) Filed: Mar. 4, 2005

(65) Prior Publication Data

US 2005/0165283 A1 Jul. 28, 2005

Related U.S. Application Data

(63) Continuation-in-part of application No. 11/042,496, filed on Jan. 25, 2005, now abandoned, which is a continuation-in-part of application No. 10/356,292, filed on Jan. 31, 2003.

(51) Int. Cl.
*A61B 1/32* (2006.01)

(52) U.S. Cl. .................................................. 600/245

(58) Field of Classification Search ................ 600/199, 600/200, 203, 212, 213, 223, 241, 245, 246
See application file for complete search history.

(56) References Cited

U.S. PATENT DOCUMENTS

| | | | |
|---|---|---|---|
| 2,296,793 A | 9/1942 | Kirschbaum | |
| 2,840,070 A | 6/1958 | Tofflemire | |
| 3,592,199 A | * 7/1971 | Ostensen | .................... 600/198 |
| 4,052,980 A | 10/1977 | Grams | |
| 4,226,228 A | 10/1980 | Shin | |
| 4,337,763 A | 7/1982 | Petrassevich | |
| 4,562,832 A | 1/1986 | Wilder | |
| 4,597,030 A | 6/1986 | Brody | |
| 4,784,150 A | 11/1988 | Voorhies | |
| 4,945,896 A | 8/1990 | Gade | |
| 5,035,232 A | 7/1991 | Lutze | |
| 5,159,921 A | 11/1992 | Hoover | |
| 5,237,985 A | 8/1993 | Hodgson | |
| 5,353,786 A | 10/1994 | Wilk | |
| 5,431,153 A | 7/1995 | Lee | |
| 5,520,611 A | 5/1996 | Rao et al. | |
| 5,558,622 A | 9/1996 | Greenberg | |
| 5,755,660 A | 5/1998 | Tyagi | |
| 5,928,139 A | 7/1999 | Koros | |
| 5,928,140 A | 7/1999 | Hardten | |

(Continued)

FOREIGN PATENT DOCUMENTS

DE 29713569 12/1997

OTHER PUBLICATIONS

European search report mailed Apr. 20, 2006.

*Primary Examiner*—Eduardo C. Robert
*Assistant Examiner*—Michael J. Araj
(74) *Attorney, Agent, or Firm*—Baker & Daniels

(57) ABSTRACT

An apparatus for illuminated retraction of a surgical cavity includes a surgical retractor having a generally tubular body forming a cannula insertable into a surgical cavity. The cannula has an inner surface defining a passage from a first end to a second end and an outer surface for abutting the margins of the surgical cavity. A light conduit includes a light emitting end for positioning adjacent to the passage to direct light into the passage.

25 Claims, 12 Drawing Sheets

U.S. PATENT DOCUMENTS

| | | |
|---|---|---|
| 5,967,971 A | 10/1999 | Bolser |
| 6,042,538 A | 3/2000 | Puskas |
| 6,080,105 A | 6/2000 | Spears |
| 6,139,493 A | 10/2000 | Koros |
| 6,193,651 B1 | 2/2001 | DeFonzo |
| 6,196,968 B1 | 3/2001 | Rydin |
| 6,210,325 B1 | 4/2001 | Bartie |
| 6,228,024 B1 | 5/2001 | Co et al. |
| 6,263,133 B1 | 7/2001 | Hamm |
| 6,322,499 B1 | 11/2001 | Evans |
| D458,680 S | 6/2002 | Engler |
| 6,428,473 B1 | 8/2002 | Leonard |
| 6,468,206 B1 | 10/2002 | Hipps |
| 6,482,153 B1 | 11/2002 | Hipps |
| 6,554,768 B1 | 4/2003 | Leonard |
| 6,591,049 B2 | 7/2003 | Williams |
| 6,676,706 B1 | 1/2004 | Mears |
| 6,895,164 B2 * | 5/2005 | Saccomanno ............... 385/146 |
| 7,223,233 B2 * | 5/2007 | Branch et al. ............... 600/212 |
| 2003/0095781 A1 | 5/2003 | Williams |
| 2003/0220547 A1 | 11/2003 | Holland |
| 2004/0143169 A1 | 7/2004 | Branch |
| 2004/0172105 A1 | 9/2004 | Vankoski |

* cited by examiner

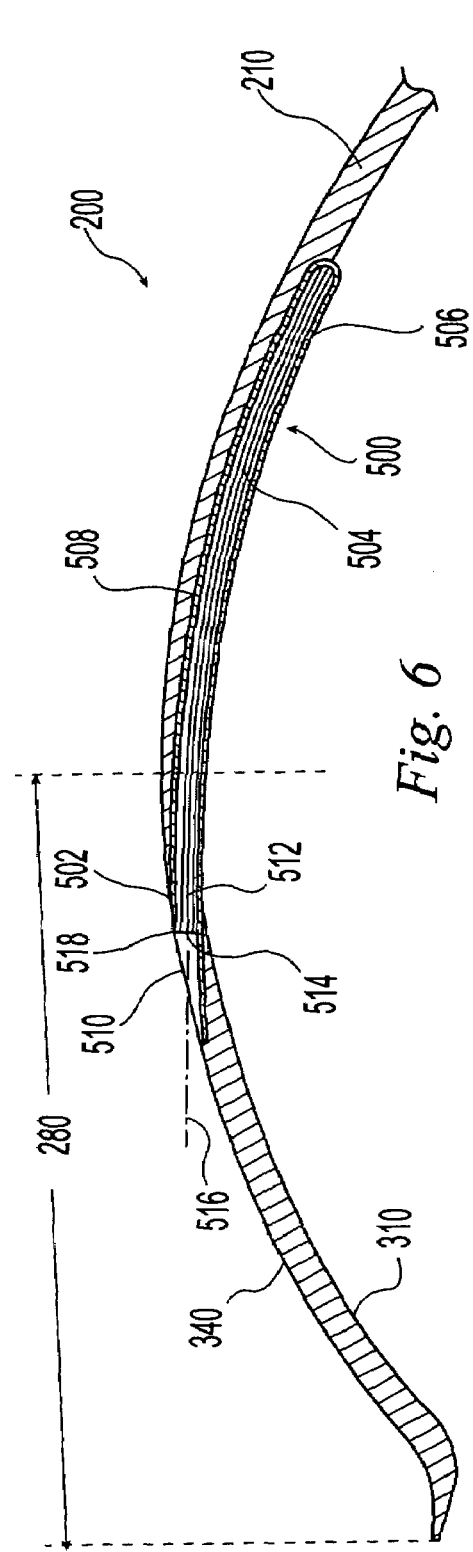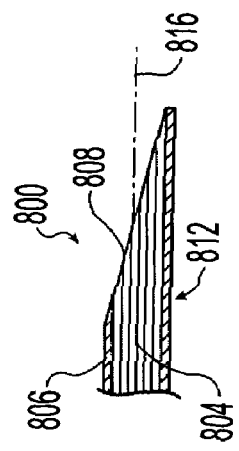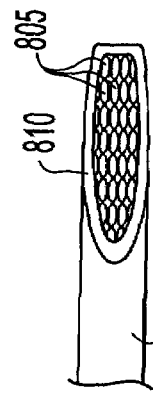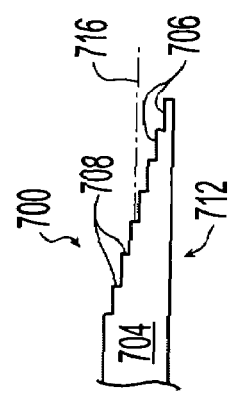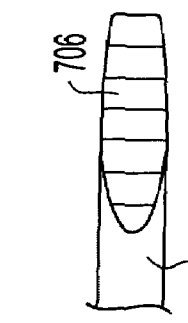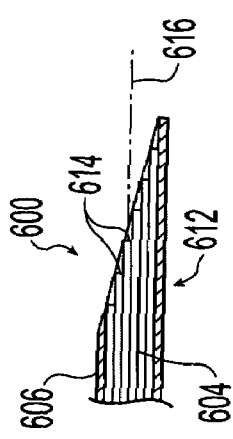

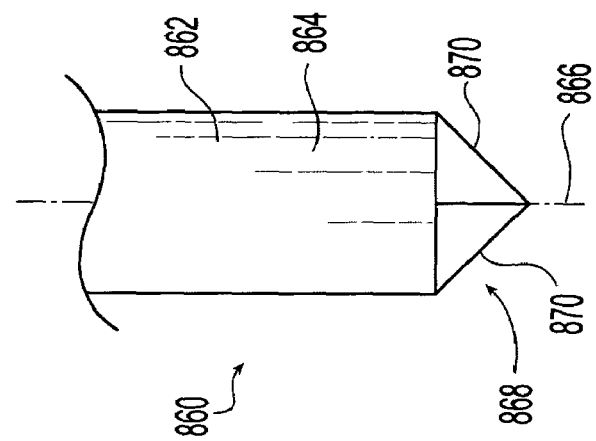
Fig. 17  Fig. 18
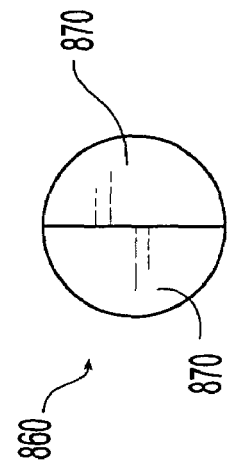
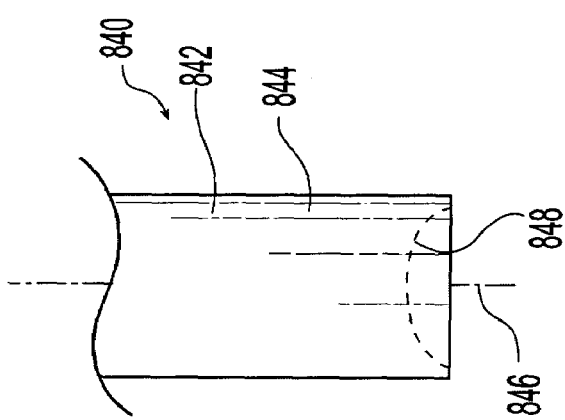
Fig. 15  Fig. 16
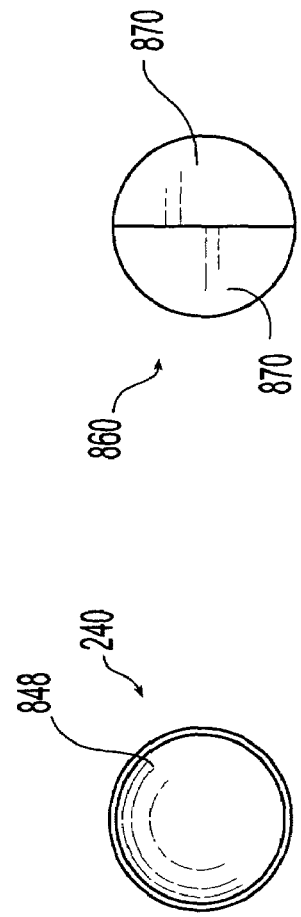
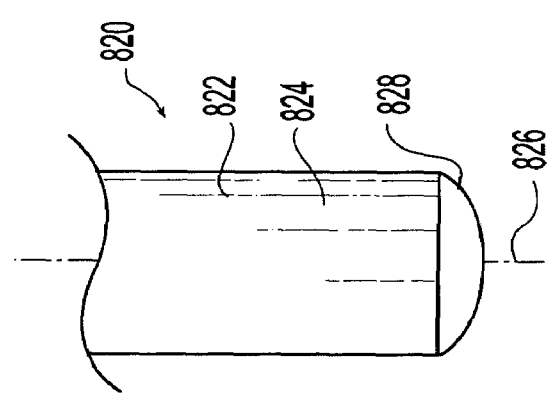
Fig. 13  Fig. 14
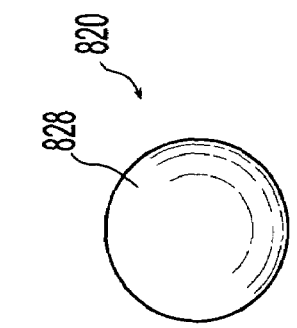

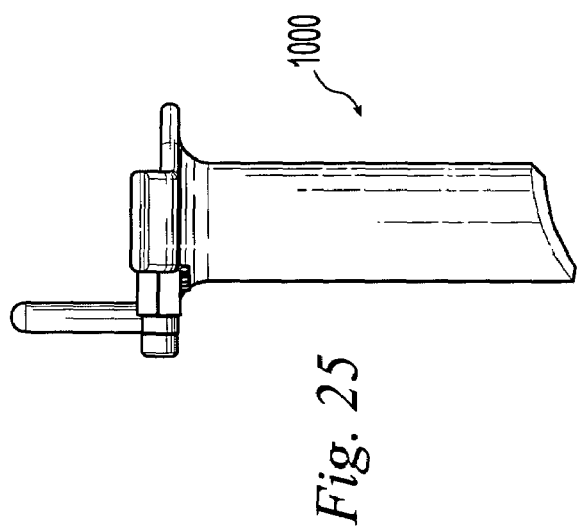
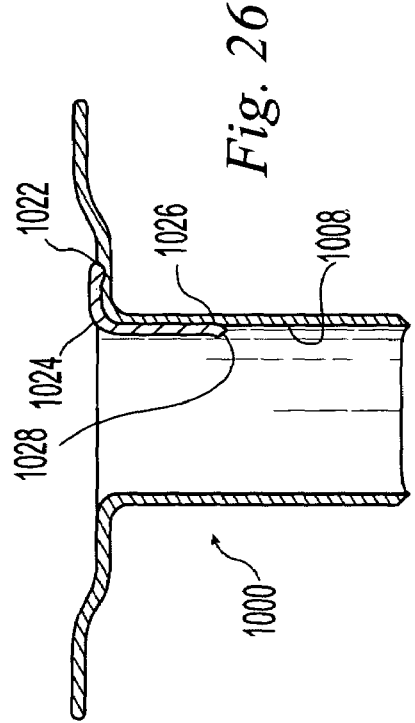
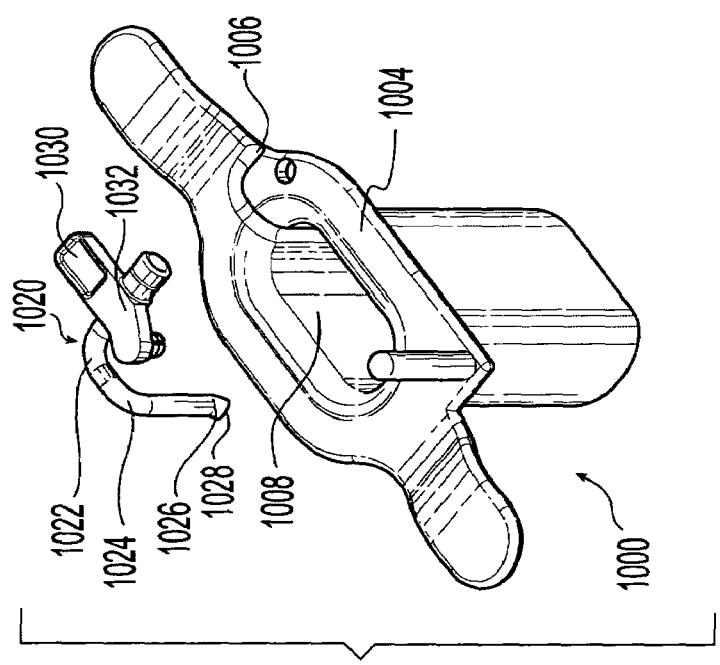
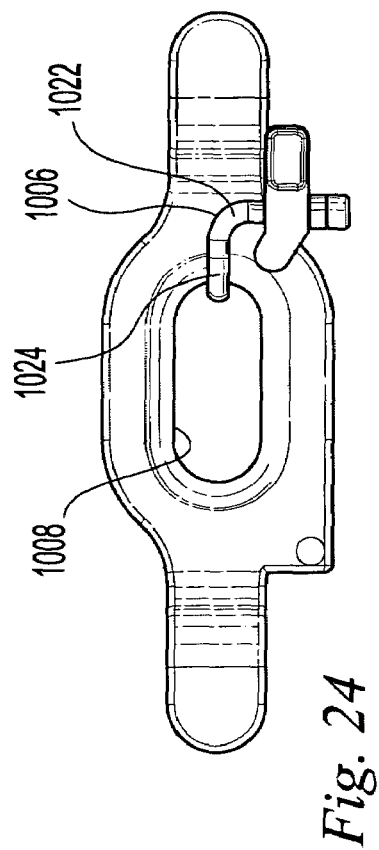

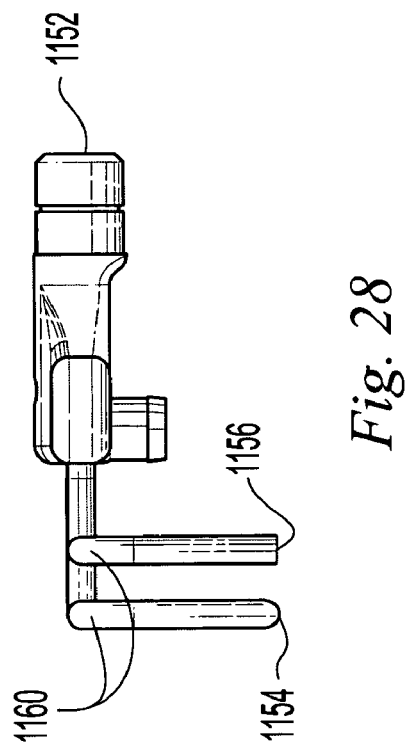
Fig. 28
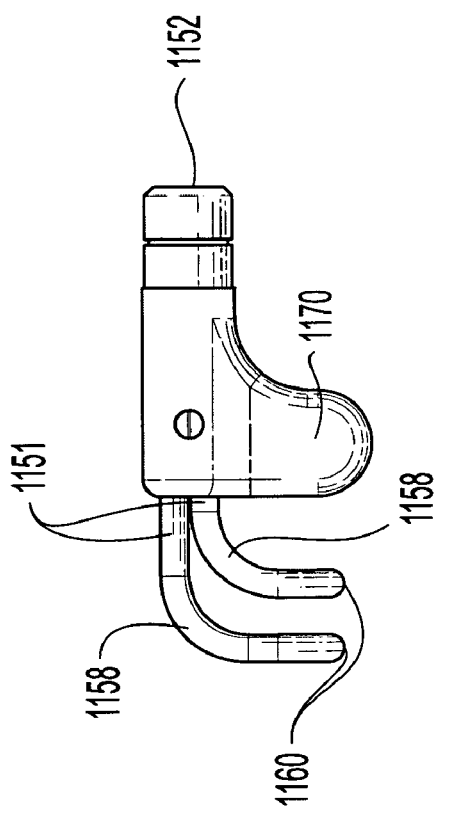
Fig. 30
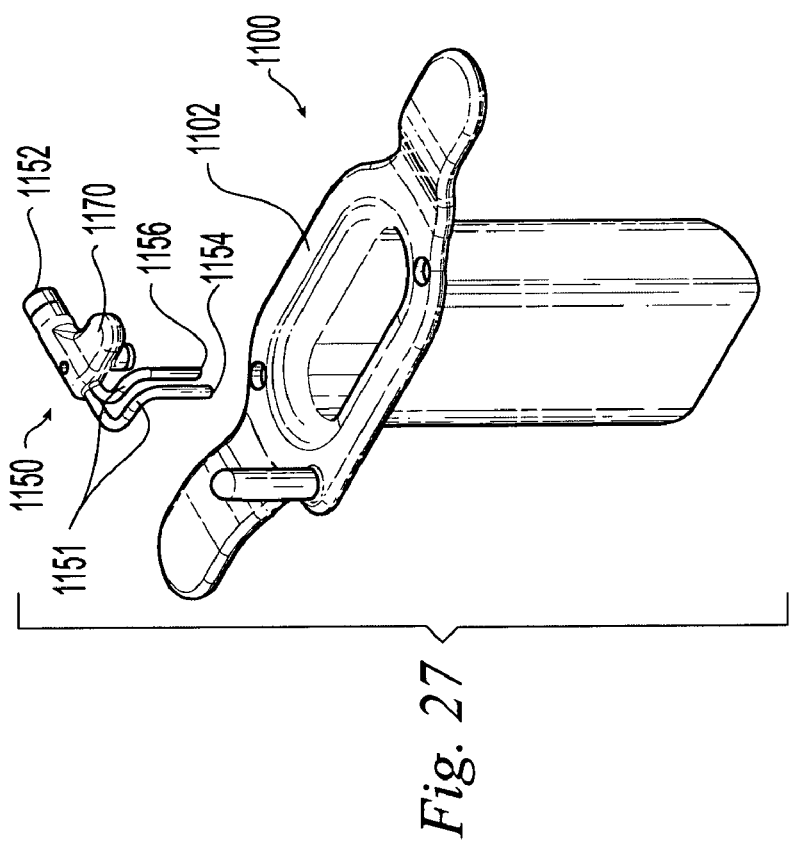
Fig. 27
Fig. 29

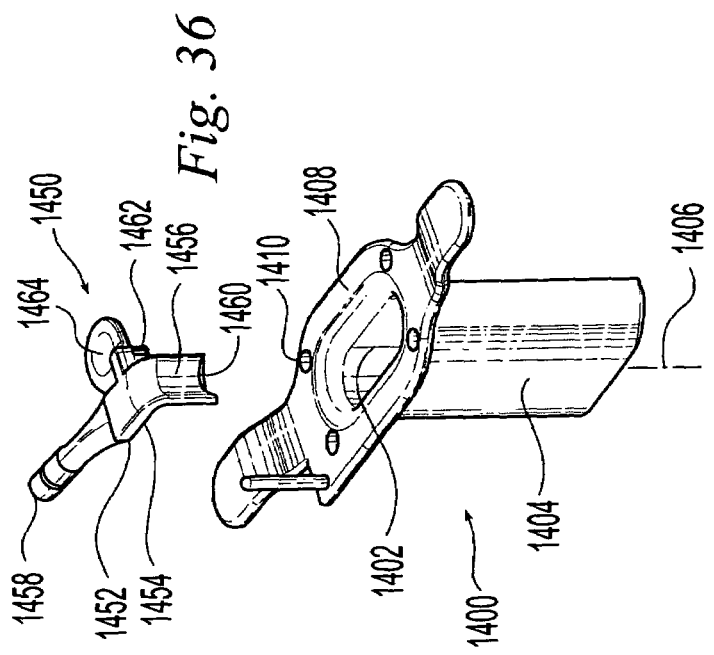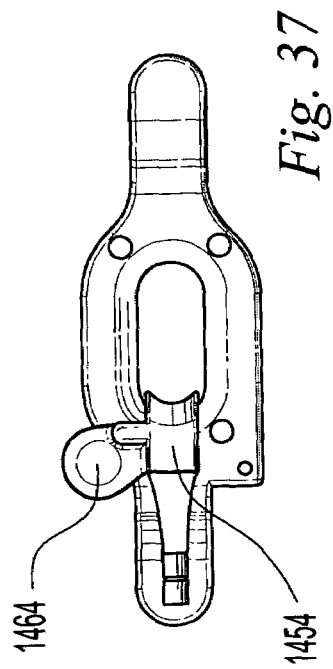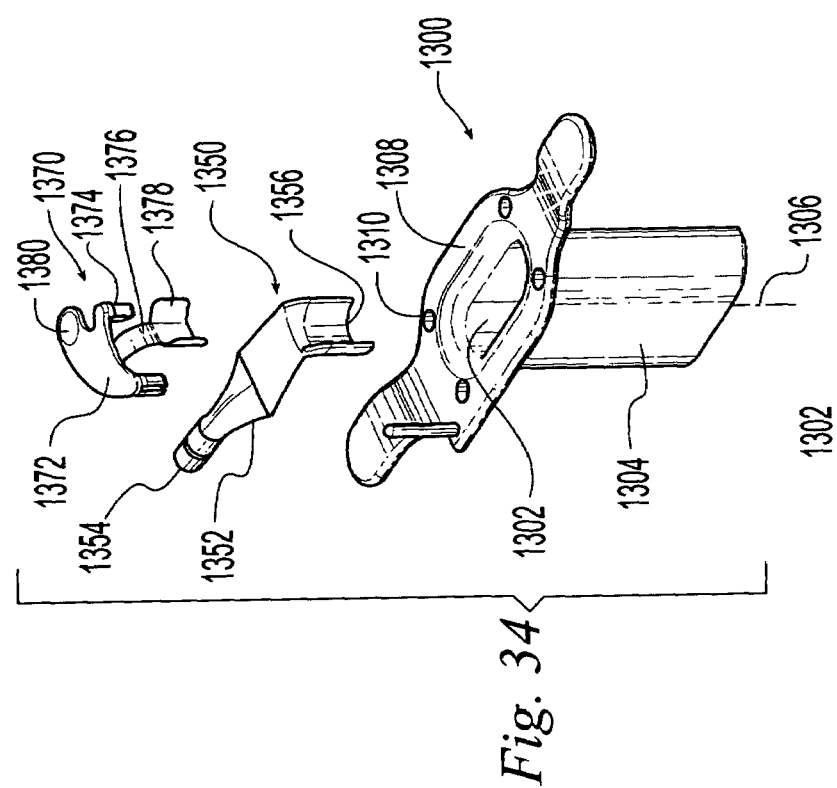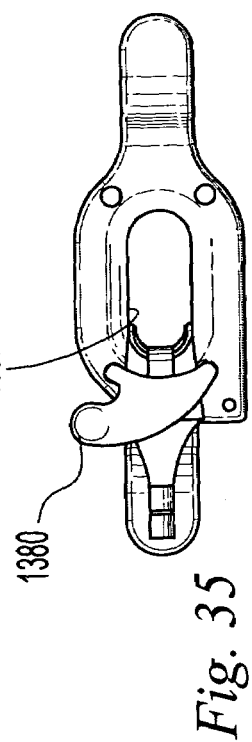

LIT RETRACTOR

CROSS-REFERENCE TO RELATED APPLICATIONS

This application is a continuation-in-part of U.S. application Ser. No. 11/042,496, filed Jan. 25, 2005 now abandoned, which is a continuation-in-part of U.S. application Ser. No. 10/356,292, filed Jan. 31, 2003.

FIELD OF THE INVENTION

The present invention relates generally to the field of medicine, and, more particularly, to illuminated surgical retractors.

BACKGROUND

In general, surgical retractors are used to push, pull, hold and/or fold skin, flesh and/or other tissue away from a site where a surgical operation or other intervention is being performed. Retractors expand the cavity or working area around the site, providing more room in which to maneuver operating and diagnostic tools. Retractors have also been used to facilitate separation of various tissues from architectures proximal to the surgical site, thereby improving access to and visibility of the site. Retractors in the form of cannulae are often used to maintain access to surgical sites in arthroscopic, laparoscopic, gynecological, and neurological procedures.

Historically, surgical retractors have been comprised of two main parts: a body or handle portion and an insertion portion or insert. The body is typically held by an operator when manipulating the retractor or coupled to a support frame that may include weights or mechanisms designed to facilitate desired movements and hold the retractor in place. The insert is suitably configured to move or grasp the desired tissues. For example, by putting a hook-shaped insert into a surgical cavity and then rotating it, surrounding tissues may be snared and then pulled away from the working environment. In the case of a cannula, the cannula typically forms a tube that is inserted into an incision. The edges of the incision abut the cannula and are retracted such that a passage to the surgical site is maintained through the center of the cannula. Not surprisingly, a single size and shape for retractors has not been practical. Indeed, a wide variety of geometries has been developed for different surgical wherein the retractor holds the body tissue out of the way while the lighting system concurrently illuminates the body cavity. However, relying on directed lighting external to a surgical cavity can be problematic due to difficulties in projecting the light in the required direction and shadows that may be cast onto the operating field. Moreover, separate retracting and lighting systems may be frustrating for an operator who is forced to manipulate both systems simultaneously, and various problems may arise as separate lighting and retracting tools get in the way of each other and cross paths with other equipment in the operating room.

Some retractor designs have sought to integrate retracting and lighting functions into a single device. However, the various complex ways of housing light sources and delivering light to the inserts in many of these illuminated or lit retractors have produced limited retractor geometries, bulky and/or heavy handles and inserts, and/or maintenance issues. Furthermore, some illuminated retractors have tended to emit narrow spot beams of light directed to rather small locations of the operating site while others have tended to emit more diffuse lighting, but often with low intensity.

Consequently, the competing needs for variety in size and geometry, directed lighting and diffuse lighting, and simplicity have tended to limit the effectiveness of historical illuminated retractors.

SUMMARY

The present invention provides a light for a surgical retractor.

In one aspect of the invention, an apparatus for illuminated retraction of a surgical cavity includes a surgical retractor having a generally tubular body forming a cannula insertable into a surgical cavity. The cannula has an inner surface defining a passage from a first end to second end and an outer surface for abutting the margins of the surgical cavity. A light conduit including a light emitting end positioned adjacent to the passage to direct light into the passage.

In another aspect of the invention, a light for a surgical retractor includes a plurality of separate, spaced apart light conduits, each conduit having a light emitting end.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 6 shows a side sectional view of the apparatus of FIG. 1, taken along line 6-6 of FIG.2, showing an alternate tip configuration;

FIG. 7 shows a detail side sectional view of the apparatus of FIG. 1 showing an alternate tip configuration;

FIG. 8 shows a detail top view of the apparatus of FIG. 7;

FIG. 9 shows a detail side sectional view of the apparatus of FIG. 1 showing an alternate tip configuration;

FIG. 10 shows a detail top view of the apparatus of FIG. 9;

FIG. 11 shows a detail side sectional view of the apparatus of FIG. 1 showing an alternate tip configuration;

FIG. 12 shows a detail top view of the apparatus of FIG. 11;

FIG. 13 shows a side view of an alternative tip configuration for the light conduit of FIG. 1;

FIG. 14 shows an end view of the tip configuration of FIG. 13;

FIG. 15 shows a side view of an alternative tip configuration for the light conduit of FIG. 1;

FIG. 16 shows an end view of the tip configuration of FIG. 15;

FIG. 17 shows a side view of an alternative tip configuration for the light conduit of FIG. 1;

FIG. 18 shows an end view of the tip configuration of FIG. 17;

FIG. 23 shows an exploded perspective view of an illustrative lit retractor in the form of a cannula;

FIG. 24 shows a top plan view of the retractor of FIG. 23;

FIG. 25 shows a side elevation view of the retractor of FIG. 23;

FIG. 26 shows a cross sectional view taken along line 26-26 of FIG. 24;

FIG. 27 shows an exploded perspective view of an illustrative lit retractor in the form of a cannula and a light conduit;

FIG. 28 shows a front elevation view of the light conduit of FIG. 27;

FIG. 29 shows a side elevation view of the light conduit of FIG. 27;

FIG. 30 shows a top plan view of the light conduit of FIG. 27;

FIG. 34 shows an exploded perspective view of an illustrative lit retractor in the form of a cannula;

FIG. 35 shows a top plan view of the retractor of FIG. 34;

FIG. 36 shows an exploded perspective view of an illustrative lit retractor in the form of a cannula; and FIG. 37 shows a top plan view of the retractor of FIG. 36.

DESCRIPTION OF THE ILLUSTRATIVE EXAMPLES

It is noted that as used throughout this disclosure and the claims, the terms "finger-releasable," "finger-releasably," and the like mean separable by a human hand(s), finger(s), and/or thumb(s)—without tools; whereas, the terms "releasable," "releasably," and the like mean separable with or without tools.

Figure 1:
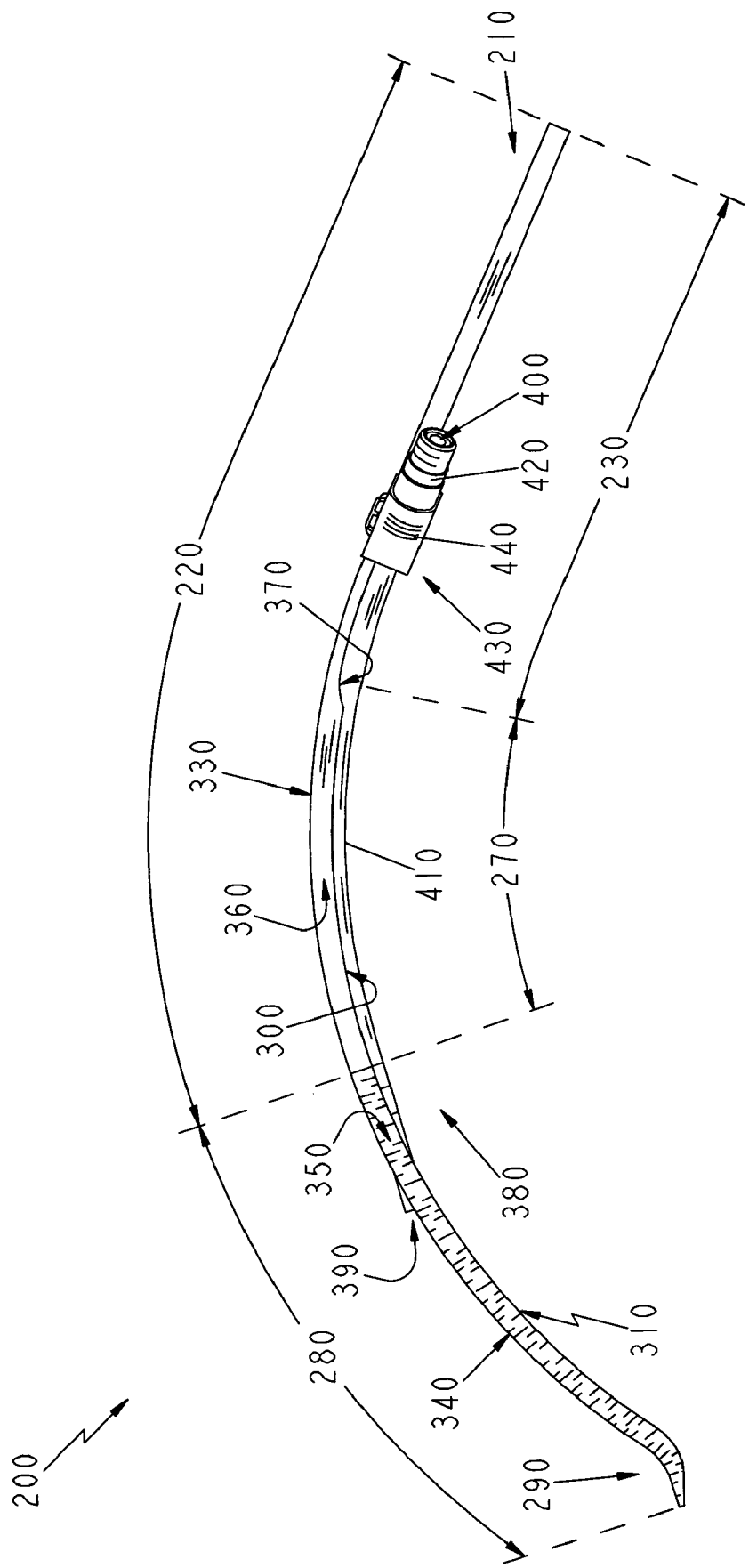
FIG. 1 shows a side (or profile) view of an exemplary apparatus according to the present invention.

FIG. 1 shows a side (or profile) view of an exemplary apparatus 200 according to the present invention. Apparatus 200 is of suitable size and weight for manipulation by hand and includes a surgical retractor 210 that is suitable for sterilization in an autoclave. In the exemplary embodiment, surgical retractor 210 is made from stainless steel. In alternative embodiments, surgical retractor 210 may be made from high temperature plastic or any other material or combination of materials suitable for use in surgical procedures. Surgical retractor 210 includes a body portion 220. Portion 220 includes a generally planar portion 230 defining an aperture or hole 240, an aperture or hole 250, and an aperture or hole 260 (see FIG. 2, FIG. 3, and FIG. 5), and further includes a generally arcuate or curved portion 270 extending from portion 230. Surgical retractor 210 further includes a generally arcuate or curved insertion portion 280 extending from portion 270. Portion 280 includes a generally arcuate or curved end portion 290. Portion 220 includes a lackluster bottom surface 300 and portion 280 includes a lustrous bottom surface 310 (see also FIG. 4. and FIG. 5). Also, portion 220 includes a lackluster top surface 330, while portion 280 includes a lustrous top surface 340. Portion 280 also includes a lustrous side surface 350 extending between surface 310 and surface 340, and further includes an opposing lustrous side surface (not shown). Meanwhile, portion 220 also includes a lackluster side surface 360 extending between surface 300 and surface 330, and further includes an opposing lackluster side surface (not shown). In the exemplary embodiment, the lustrous surfaces (e.g., 340, 350, 310) are produced by suitably color buffing portion 280 in a known manner and the lackluster surfaces (e.g., 330, 360, 300) are produced by suitably mass finishing portion 220 in a known manner. Additionally, portion 280 defines a generally ovular aperture or hole 364 extending between surface 310 and surface 340 (see FIG. 3 and FIG. 5). Surface 300, surface 310, and surface 360 define a groove or channel 370 extending between surface 360 and hole 364 (see FIG. 5), while surface 340 defines a groove or channel 374 that also communicates with hole 364 (see FIG. 2).

Apparatus 200 also includes a light conduit 380 having a side-view geometry or profile substantially conforming to that of surgical retractor 210. Conduit 380 includes an end 390, an end 400, and an optional casing or sheath 410. Sheath 410 extends through channel 370 and hole 364 such that end 390 protrudes from an intermediate portion of channel 374 (see also FIG. 2, FIG. 4, and FIG. 5). Further, sheath 410 includes a lustrous outer surface 416 extending from end 390 and a lackluster outer surface 418 extending from surface 416 to end 400 (see FIG. 3, FIG. 4, and FIG. 5).

In general, conduit 380 is suitable for use in surgical procedures and configured to transmit externally generated light from end 400 to end 390. Accordingly, conduit 380 includes one or more fiber optic cables and/or any other suitable light transmitting materials. The light transmitting materials may be in the form of a single cable or filament such as a glass or plastic rod. The filament may be molded or otherwise formed into a desired cross-sectional and longitudinal shape. The single filament may alone form the conduit 380 or the single filament may be housed in optional sheath 410 to protect the filament, provide additional rigidity or flexibility, and/or improve the light transmission and/or dispersion of the conduit 380. Alternatively, the light transmitting materials may be in the form of a plurality of filaments such as a plurality of glass or plastic filaments. The plurality of filaments may be loosely gathered and constrained in a desired shape by placing them within optional sheath 410. The filaments may also be formed into a self-supporting structure such as by adhering them to one another with an adhesive and/or by fusing them with heat and/or pressure. The multifilament structure may then be optionally housed in sheath 410. The conduit 380 includes a coupling member 420 fixedly housing a portion of sheath 410 proximal to end 400. Member 420 is configured in a known manner for finger-releasably coupling conduit 380 to an external light source.

In the exemplary embodiment, conduit 380 is reusable and suitable for sterilization in an autoclave. Accordingly, sheath 410 is a rigid stainless steel pipe with lustrous outer surface 416 produced by suitable color buffing and lackluster outer surface 418 produced by suitable mass finishing. In alternative embodiments, the various components of conduit 380 may be made from high temperature plastic and/or any other material or combination of materials suitable for use in surgical procedures and sterilization in an autoclave, and sheath 410 may or may not be flexible. It is noted, however, that in some alternative embodiments conduit 380 may be disposable and, accordingly, in such alternative embodiments all of the components of conduit 380 may be made of relatively inexpensive low temperature acrylics or polymers.

Apparatus 200 further includes a bracket 430 that finger-releasably couples conduit 380 to surgical retractor 210.

Figure 2:
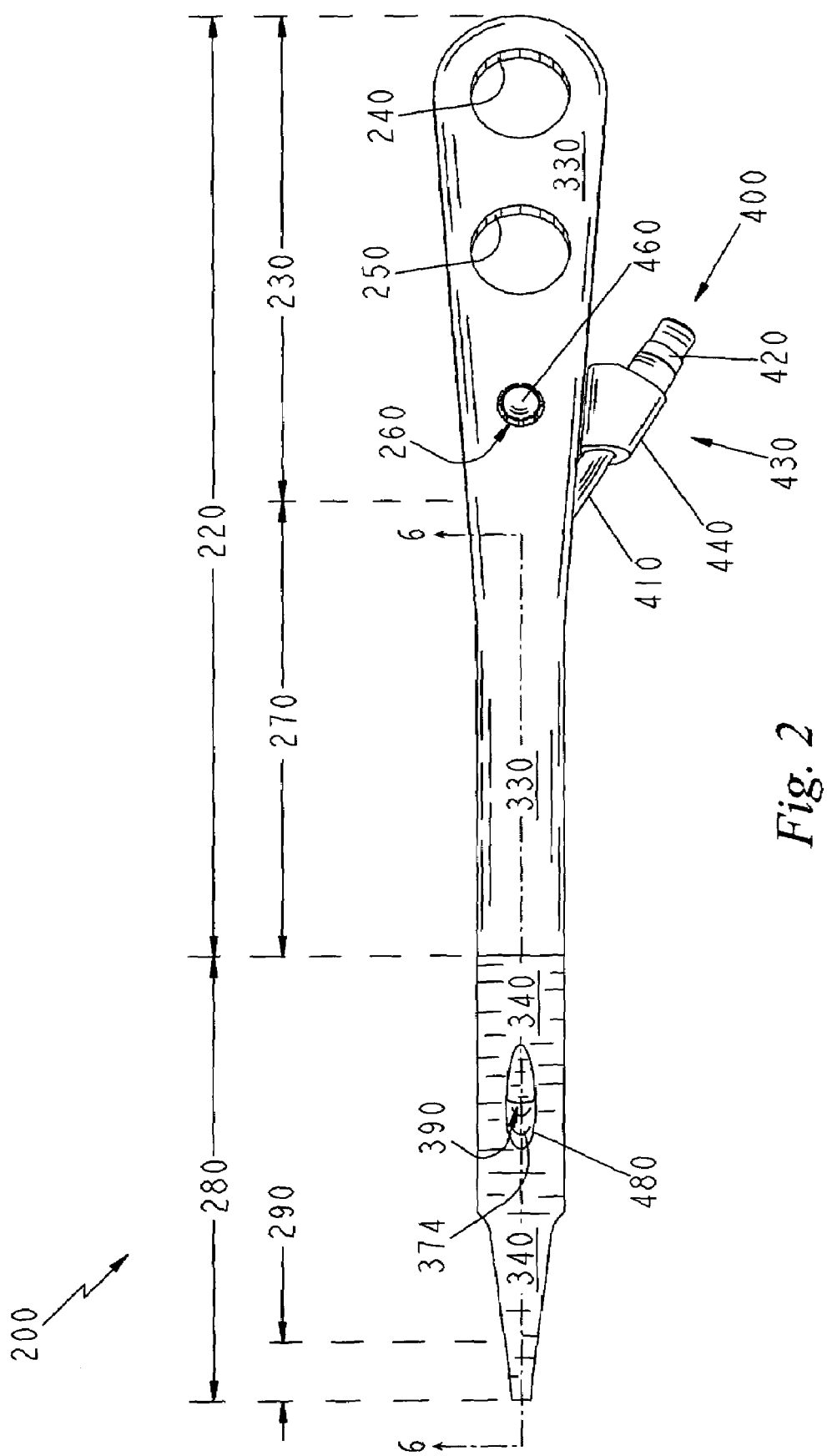
FIG. 2 shows a top view of the exemplary apparatus.
Figure 3:
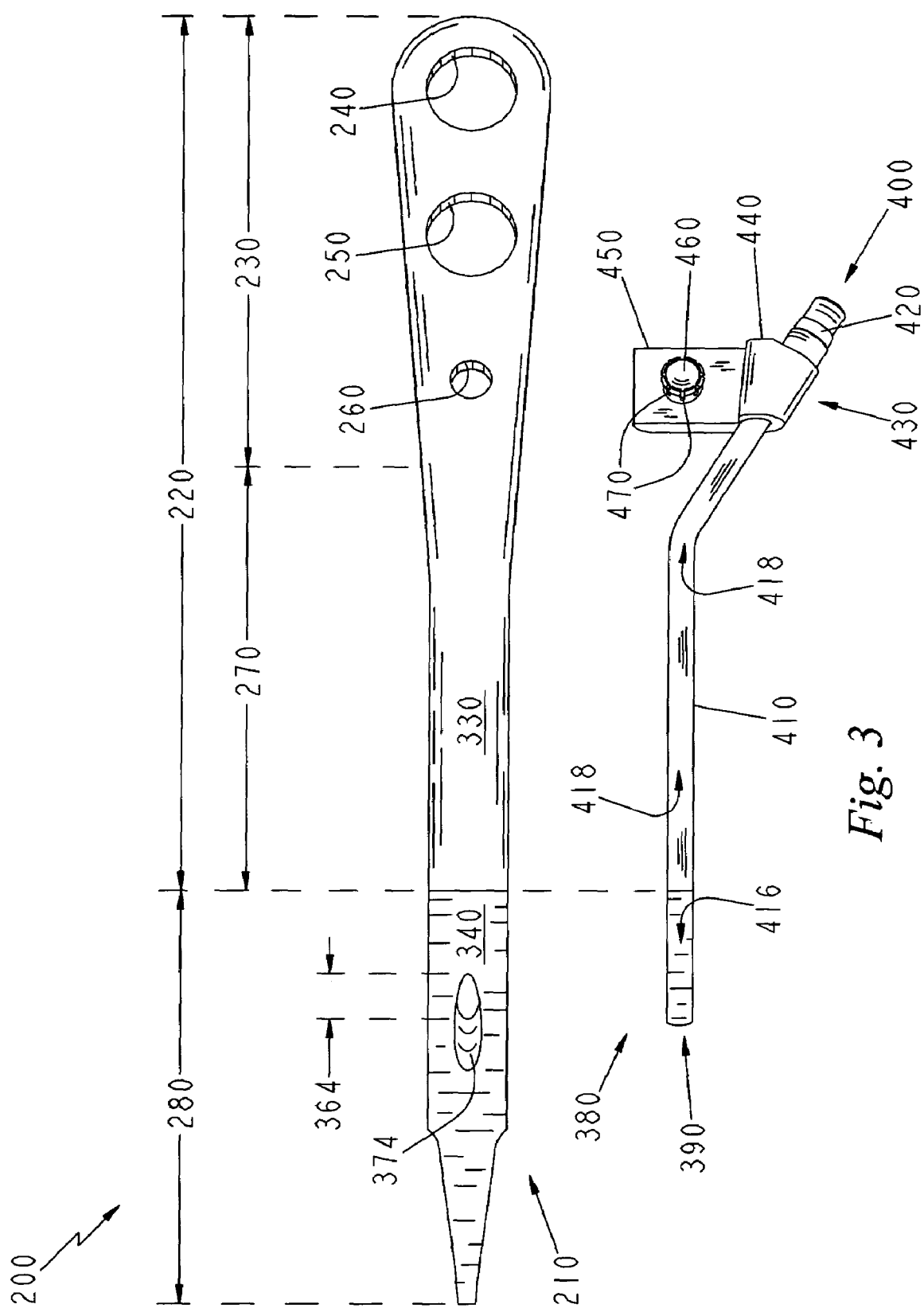
FIG. 3 shows a laterally exploded top view of the exemplary apparatus.

Bracket 430 includes a sleeve portion 440 fixedly housing a portion of sheath 410 of conduit 380 proximal to end 400 and distal to end 390 (see also FIG. 2 and FIG. 3). Bracket 430 further includes a generally planar flange portion 450 extending laterally underneath portion 230 of surgical retractor 210 proximal to surface 300 (see FIG. 3, FIG. 4, and FIG. 5). Bracket 430 also includes a button or peg 460, having a plurality of slits 470 therein, extending upward from flange portion 450 and snugly fitted into hole 260 of surgical retractor 210 such that peg 460 (and thus bracket 430 and conduit 380) is finger-releasably coupled to surgical retractor 210 (see FIG. 2 and FIG. 3). It should be appreciated, however, that various components in alternative embodiments may include a screw/socket arrangement, a lever operated latch, or any other suitable alternative coupling or couplings for releasably coupling conduit 380 to surgical retractor 210, including (in some embodiments) a coupling that releasably couples conduit 380 to surgical retractor 210 but does not finger-releasably couple conduit 380 to surgical retractor 210.

FIG. 2 shows a top view of exemplary apparatus 200. Hole 240, hole 250, hole 260, and channel 374 are discernible in FIG. 2. Additionally, FIG. 2 shows that channel 374 includes a generally ovular rim 480. Portion 220, portion 230, portion 270, portion 280, portion 290, surface 330, surface 340, end 390, end 400, sheath 410, member 420, bracket 430, portion 440, and peg 460 are discussed above in connection with FIG. 1.

FIG. 3 shows a laterally exploded top view of exemplary apparatus 200. Among other things, surgical retractor 210 (including portion 220, portion 230, hole 240, hole 250, hole 260, portion 270, portion 280, surface 330, surface 340, hole 364, and channel 374), conduit 380 (including end 390, end 400, sheath 410, surface 416, surface 418, and member 420), and bracket 430 (including portion 440, portion 450, peg 460, and slits 470)—all discussed above in connection with FIG. 1—are discernable in FIG. 3.

Figure 4:
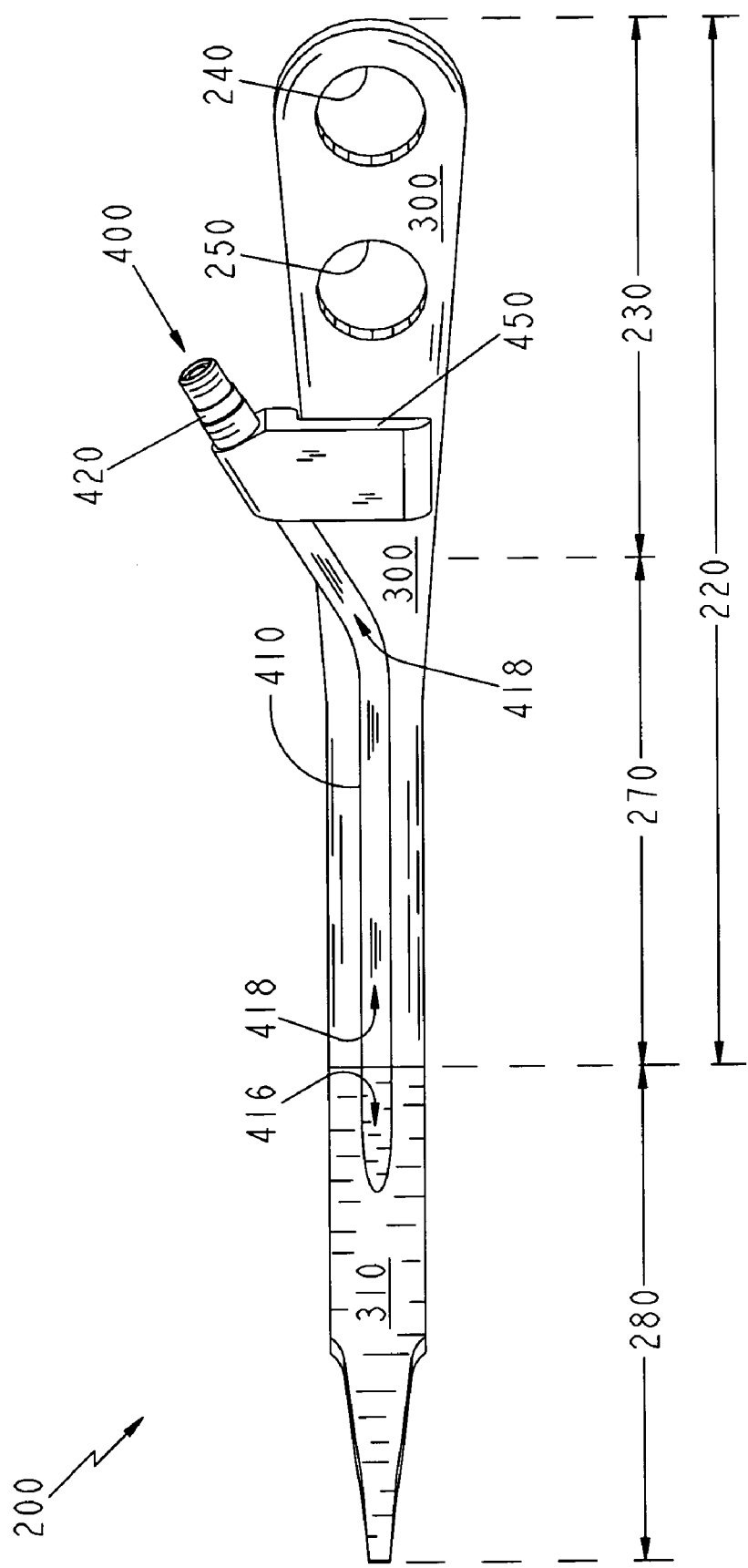
FIG. 4 shows a bottom view of the exemplary apparatus.

FIG. 4 shows a bottom view of exemplary apparatus 200. Among other things, portion 220, portion 230, portion 270, portion 280, hole 240, hole, 250, surface 300, surface 310, end 400, sheath 410, surface 416, surface 418, and member 420—all discussed above in connection with FIG. 1—are discernable in FIG. 4.

Figure 5:
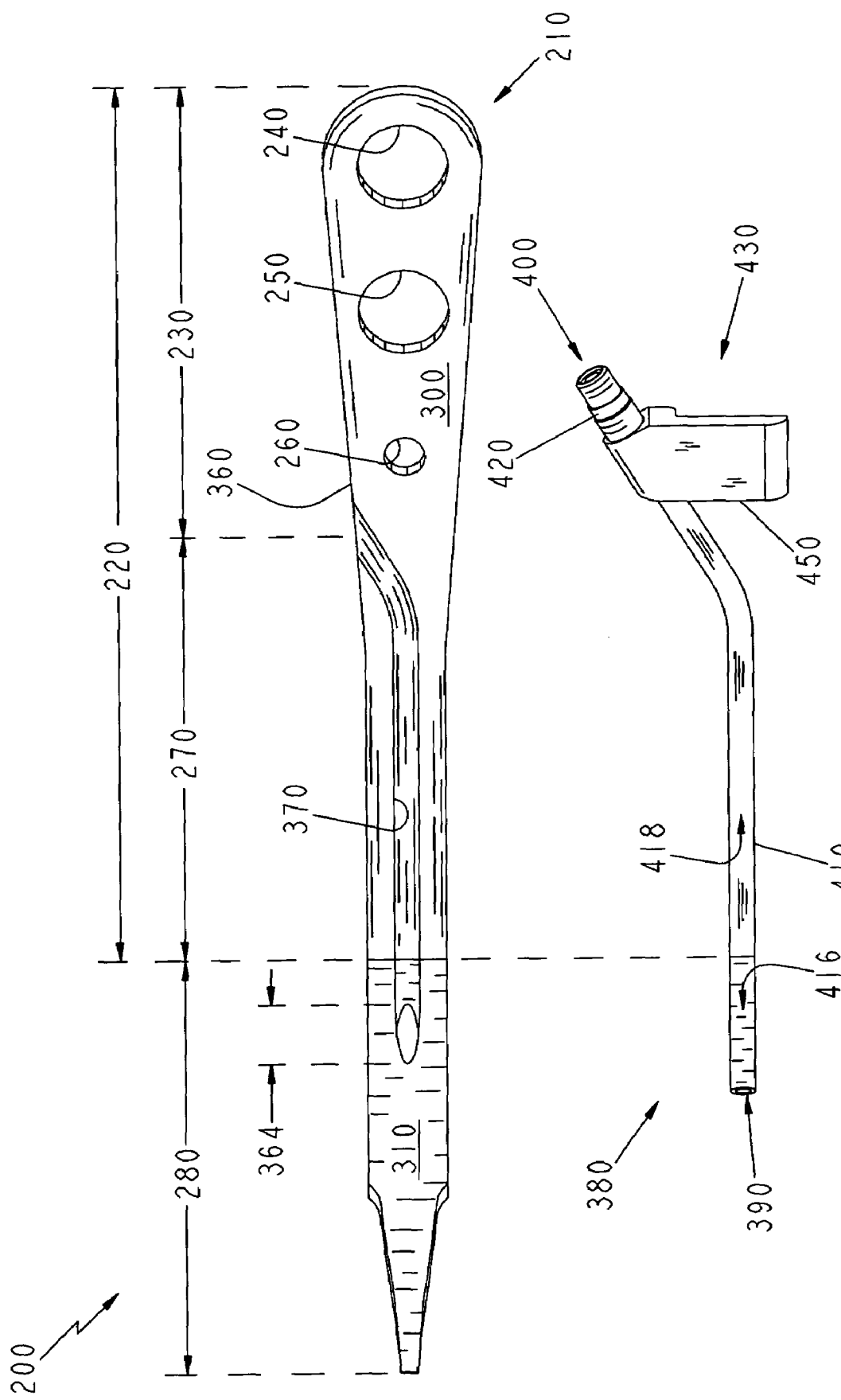
FIG. 5 shows a laterally exploded bottom view of the exemplary apparatus.
Figure 20:
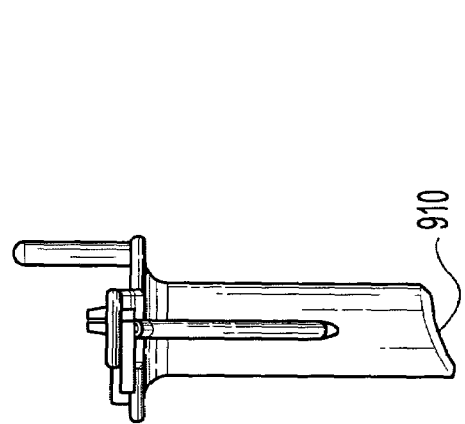
FIG. 20 shows a top plan view of the retractor of FIG. 19.

FIG. 5 shows a laterally exploded bottom view of exemplary apparatus 200. Among other things, surgical retractor 210 (including portion 220, portion 230, hole 240, hole 250, hole 260, portion 270, portion 280, surface 300, surface 310, surface 360, hole 364, and channel 370), conduit 380 (including end 390, end 400, sheath 410, surface 416, surface 418, and member 420), and bracket 430 (including portion 450)—all discussed above in connection with FIG. 1—are discernable in FIG. 5.

In operation of exemplary apparatus 200, member 420 of light conduit 380 is coupled to a suitable external light source and insertion portion 280 of surgical retractor 210 is inserted into a surgical cavity. Body portion 220 is used to grasp and manipulate surgical retractor 210 as desired. It should be appreciated that the low profile and light weight of exemplary apparatus 200 facilitates its manipulation. In any event, light from the external source is emitted from end 390 of light conduit 380. Channel 374 focuses some of this light into somewhat of a spotlight like beam. Insertion portion 280 is suitably maneuvered to direct the focused light into a desired portion of the surgical cavity. Meanwhile, one or more of the lustrous surfaces (e.g., 340, 350, 310) also reflect a portion of the light present in the surgical cavity, thereby dispersing some of the light to generally illuminate another portion or portions of the surgical cavity at a somewhat lower intensity than the area illuminated by the focused light. Consequently, general or somewhat diffuse lighting of the surgical cavity is provided concurrently with more focused lighting of relatively higher intensity.

For additional dispersion and/or additional focused lighting, additional surgical retractor 210 and/or apparatus 200 are inserted into the surgical cavity as desired. In such cases, various lustrous surfaces of the various surgical retractor 210 may cooperate somewhat to reflect light amongst themselves, thereby enhancing the dispersive effect while maintaining the availability of one or more directable beams.

To facilitate cleaning of apparatus 200 or use of surgical retractor 210 without light conduit 380, conduit 380 is released from surgical retractor 210 by pushing peg 460 of bracket 430 out of hole 260 of surgical retractor 210 with a finger or thumb, and conduit 380 is removed from channel 370 and channel 374 by moving bracket 430 generally down and away from surgical retractor 210 and by pulling bracket 430 generally away from hole 364 such that end 390 of conduit 380 is withdrawn from channel 374 through hole 364, thereby separating conduit 380 and bracket 430 from surgical retractor 210.

FIGS. 6-18 show alternative configurations for the tip of the light conduit in which the light conduit terminates at an end that lies flush with, or is recessed below, the top surface 340 of the insertion portion 280 of the retractor 210. The end may be generally planar or it may be a simple or complex curve. Preferably, the end corresponds to the shape of the top surface 340 of the retractor 210 adjacent the hole 364 where the end resides. If the top surface 340 is curved but of a relatively large radius, an angled planar end will be a close approximation of this surface and may be simpler and less expensive to manufacture. By having the conduit end flush, or below flush, with the top surface 340 of the retractor 210, the apparatus 200 presents a smooth surface such that other surgical components, including instruments and implants, will not catch on the apparatus 200 as they are passed into and out of the surgical site. Likewise, this arrangement provides the largest possible opening between the retractor 210 and the rest of the surgical site. In each of these examples, a sheath may be included if it provides more desirable light transmission properties, more desirable flexibility or rigidity, and/or protection of the conduit. Also, the sheath may be omitted to lower cost and/or to maximize the amount of light transmission area within a given available space. The conduits in these examples may include one or more light transmitting filaments for transmitting light to the end.

In typical use, the insertion portion 280 of the retractor 210 is inserted into a surgical cavity with the bottom surface 310 abutting the margins of the surgical cavity to retract the margins and enlarge the cavity opening. The top surface 340 faces away from the margins of the cavity. The light conduit emits light through the hole 364 in the top surface 340 to illuminate the surgical cavity.

The exemplary conduit 500 of FIG. 6 includes a plurality of light transmitting filaments 504 contained within an optional sheath 506. The sheath 506 includes a wall 508 terminating at an angled light emitting end 502. An angled opening 510 extends through the sheath wall 508 to allow light to exit the sheath 506 at the end 502. The filaments 504 terminate in a cylindrical end portion 512 having a longitudinal axis 516 and an end face 514 normal to the axis 516 and contained within the sheath 506. However, it is anticipated that the end portion 512 and/or the conduit 500 may have non-cylindrical shapes as well such as rectangular, oval, non-rectangular polygonal, and/or other suitable shapes. The end portion 512 terminates at the distal edge 518 of opening 510 so that the filaments 504 do not extend beyond the outer wall 508 of the sheath 506 and consequently so that they do not extend beyond the top surface 340 of the retractor 210. Light is projected from the end portion 512 to illuminate the surgical site. By recessing the light transmitting filaments 504 within the sheath 506, the sheath 506 can include an angled end while maintaining a normal end face 514 on the filaments 504 to preserve maximum light transmission out of the conduit 500 along the axis 516.

The exemplary conduit 600 of FIGS. 7 and 8 includes a plurality of light transmitting filaments 604 contained within an optional sheath 606. The sheath terminates in an angled opening 610 similar to the configuration of FIG. 6. The filaments 604 terminate in an elongate end portion 612 having a longitudinal axis 616. The filaments 604 are terminated in a cascading or stair-step configuration so that each filament 604 extends as far as possible without extending beyond the opening 610. Each filament 604 terminates in an end face 614 normal to the axis 616 for maximum light transmission out of the conduit 600 along the axis 616. The filament ends 614 may more or less closely approximate the shape of the top surface 340 of the retractor 210 depending on how fine the individual filaments 604 are. An area within the surgical site that is illuminated beyond the end 602 of the conduit 600 will experience both relatively more diffuse and relatively more focused light from the conduit 600 of FIGS. 7 and 8. The light exiting from filaments 604 terminating closer to the end 602 disperses less by the time it reaches the surgical site than light exiting from filaments 604 terminating further from the end 602. Therefore, general or relatively more diffuse lighting of the surgical site is provided by the filaments 604 terminating further from the end 602 and spot or relatively more focused lighting of the surgical site is provided by the filaments 604 terminating closer to the end 602.

The exemplary conduit 700 of FIGS. 9 and 10 includes a single light transmitting filament 704 for transmitting light to an elongate end portion 712 having a longitudinal axis 716. The filament 704 is terminated by forming a series of stair steps 706 each having an end face 708 normal to the longitudinal axis 716. The end 702 may more or less closely approximate the shape of the top surface 340 of the retractor 210 depending on how finely or coarsely the stair steps 706 are formed. The steps may be equal to approximate a planar angled surface or they may be unequal to approximate a curved surface. The normal end faces 708 provide for maximum light transmission out of the conduit along the axis 716 while the stair step arrangement provides an illumination pattern similar to that of the example of FIGS. 7 and 8. The exemplary embodiment of FIGS. 9 and 10 omits the optional sheath shown in the prior examples.

The exemplary conduit 800 of FIGS. 11 and 12 includes a plurality of light transmitting filaments 804 contained within an optional sheath 806. The sheath 806 terminates in an angled opening 810 similar to the configuration of FIG. 6. The filaments 804 terminate in an elongated end portion 812 having a longitudinal axis 816. However, in the exemplary embodiment of FIGS. 11 and 12, the filaments 804 each terminate at an angled surface 805 corresponding to the angle of the opening 810. For example; the filaments 804 may be cut and ground at an angle. The resulting conduit 800 will transmit less light along the axis 816 than the prior examples because the angled surfaces 805 tend to reflect more light back into the conduit 800 than do the normal surfaces of the preceding examples. However, the conduit 800 of FIGS. 11 and 12 can provide a continuous, smooth surface 808 flush with the top surface 340 of the retractor 210 so that there are no edges, holes, or projections to interfere with the surgical procedure. A single filament 804 may be provided having a smoothly angled end surface 805 as well.

The illustrative conduit 820 of FIGS. 13 and 14 includes a single filament 822. The filament 822 includes an end portion 824 having a longitudinal axis 826 and terminating in an end surface 828. The end surface 828 is convexly shaped to focus the light emitted from the conduit 820. The end surface may be shaped by molding, grinding, and/or other suitable shaping methods. By matching the focal length of the end surface 828 to the length of the insertion portion 280 of the retractor 210 a focused spot of light may be provided to the surgical cavity. By making the focal length significantly longer or shorter than the length of the insertion portion 280, unfocused, diffuse lighting may be provided to the surgical cavity. While the illustrative conduit 820 includes a single filament 822, the conduit 820 may also be made of a plurality of smaller filaments. In such an arrangement, the filaments may be adhered together and then ground and polished to form the convex end surface 828.

The illustrative conduit 840 of FIGS. 15 and 16 includes a single filament 842. The filament 842 includes an end portion 844 having a longitudinal axis 846 and terminating in an end surface 848. The end surface 848 is concavely shaped to diverge the light emitted from the conduit 840 to produce diffuse lighting in the surgical cavity. The end surface 848 may be shaped by molding, grinding, and/or other suitable shaping methods. While the illustrative conduit 840 includes a single filament 842, the conduit 840 may also be made of a plurality of smaller filaments. In such an arrangement, the filaments may be adhered together and then ground and polished to form the concave end surface 848.

The illustrative conduit 860 of FIGS. 17 and 18 includes a single filament 862. The filament 862 includes an end portion 864 having a longitudinal axis 866 and terminating in a faceted end surface 868. Each facet 870 will emit light in a direction normal to the facet 870 such that multiple beams of light may be emitted from a single conduit 860 to illuminate the surgical cavity. The facets 870 may be provided in any number and they may be convex, flat, concave, and/or otherwise shaped to provide a variety of lighting effects from highly focused spot beams to highly diffuse area illumination. The multiple facets may be similarly shaped to provide similar kinds of illumination or they may be differently shaped to provide different kinds of illumination. In the illustrative conduit 860, the end surface 868 includes a pair of flat facets 870 angled relative to one another to produce two beams of light diverging from one another. The facets 870 may be angled such that the beams overlap as they diverge from the flat faces to provide broad illumination with more light in the center of the illumination pattern. While the illustrative conduit 860 includes a single filament 862, the conduit 860 may also be made of a plurality of smaller filaments with some of the filaments providing light to one facet 870 and others of the filaments providing light to another facet 870.

Figure 21:
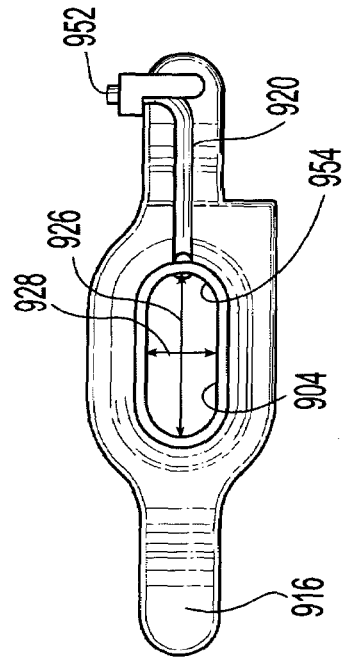
FIG. 21 shows a side elevation view of the retractor of FIG. 19.

FIGS. 19-22 illustrate a surgical retractor in the form of a cannula 900 including a generally tubular body 902 having an inner surface 904 defining a passage along an axis 906 from a first end 908 to a second end 910, and an outer surface 912 for abutting the edges of an incision. The cannula 900 includes a flange 914 extending radially outwardly from the first end 908 and at least one handle 916 extending radially outwardly from the flange 914. The flange 914 and handle 916 are used to grasp and manipulate the cannula 900. The second end 910 of the cannula 900 may be shaped to conform to a portion of a patient's anatomy, such as a vertebral body as best seen FIG. 20. The illustrative cannula 900 forms a passage having a cross sectional aspect ration greater than one, as seen in FIG. 21, such that its width 926 is greater than its height 928. The illustrative cannula 900 includes a pair of handles 916 aligned with the cannula width 926 so that the cannula 900 may be easily grasped with two hands and manipulated while keeping the width 926 of the cannula 900 aligned with a surgical site such as an intervertebral space. The cannula 900 includes an attachment post 930 for connecting the cannula to a support frame (not shown) to maintain its position.

The cannula 900 is provided with a light conduit 950 similar to that illustrated in FIGS. 1-6. The light conduit 950 includes a first end 952 and a second end 954. The conduit 950 is configured to transmit externally generated light from the first end 952 to the second end 954. The second end 954 is positioned adjacent to the cannula 900 passage to direct light into the passage. A bracket 956 is attached to a portion of the light conduit 950 and includes a peg 958 having a plurality of slits 959 separating the peg into resilient fingers. The light conduit is coupled to the cannula 900 by press fitting the peg 958 into a hole 918 provided in the handle 916. A channel 920 extends tangentially along the lower surface of the handle 916 near the hole 918, radially along the lower surface of the flange 914 toward the cannula body 902, and longitudinally along the outer surface 912 of the cannula from near the first end 908 toward the second end 910 to receive the light conduit 950. The channel 920 terminates at a hole 922 extending from the outer surface 912 to the inner surface 904 of the cannula 900. The light conduit 950 includes first, second, and third bends 960, 962, 964 such that it traverses a non-planar, three dimensional path corresponding to the channel 920. A fourth bend 966 near the second end 954 of the light conduit permits the second end 954 of the light conduit 950 to enter the hole 922 to direct light into the passageway defined by the inner surface 904 of the cannula 900. With the light conduit 950 positioned in the channel 920 and the first end 952 secured to the handle 916 by the bracket 956, the light conduit is stably attached to the cannula 900. By recessing the light conduit 950 in the channel 920, the overall bulk of the apparatus is reduced. The three dimensional path of the illustrative conduit 950 and channel 920 allow a light source to be connected tangentially to the conduit 950 near the level of the first end 908 while the light is delivered radially into the passage through the hole 922 toward the second end 910. Thus a cable from a light source can be directed transverse to the handle 916 for the convenience of the operator if desired.

Figure 22:
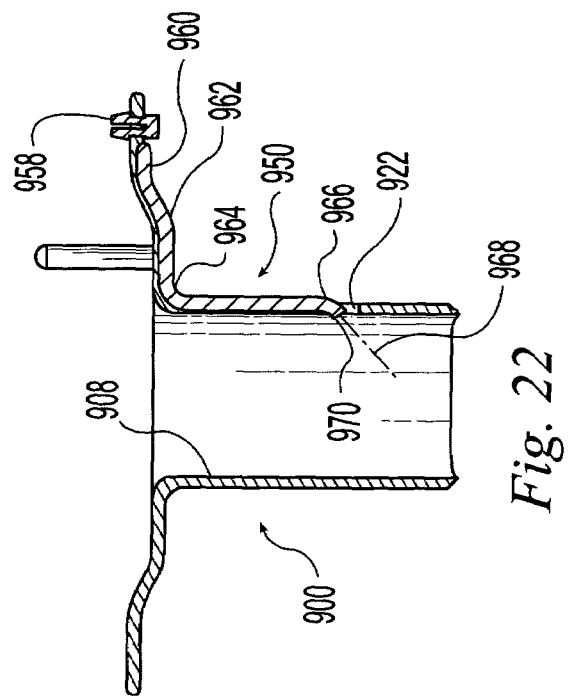
FIG. 22 shows a cross sectional view taken along line 22-22 of FIG. 20.
Figure 19:
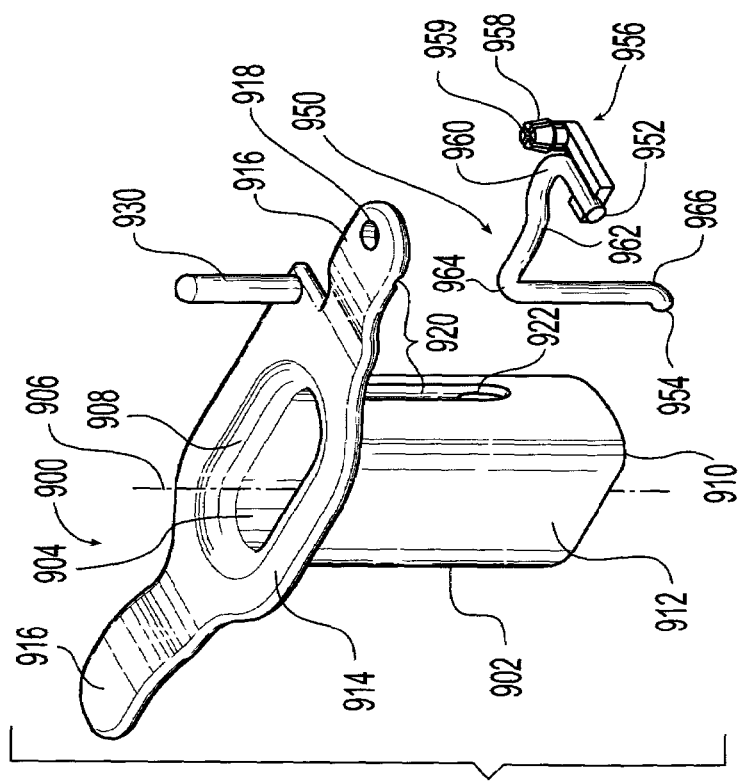
FIG. 19 shows an exploded perspective view of an illustrative lit retractor in the form of a cannula.

The light conduit 950 includes a light transmission axis 968 (FIG. 22). In the illustrative light conduit of FIGS. 19-22, the second end 954 is angled downwardly into the cannula 900 and the end surface 970 is ground to form a flat surface normal to the axis 968 similar to the apparatus of FIGS. 1-5. The light conduit 950 may be formed of a single filament or multiple filaments, it may include an optional sheath, and the second end 954 may project from the inner surface 904 (as shown), be flush with the inner surface 904, or be recessed below the inner surface 904 as described relative to FIGS. 6-12. Furthermore, the second end 954 may have any suitable tip geometry, including but not limited to those of FIGS. 6-18.

FIGS. 23-26 illustrate a cannula 1000 and light conduit 1020 similar to those of FIGS. 19-22. However, the cannula 1000 of FIGS. 23-26, includes an attachment hole 1002 in the flange 1004 and the channel 1006 extends tangentially and radially along the upper surface of the flange 1004 and longitudinally down the inner surface 1008 of the cannula 1000. The light conduit 1020 includes first and second bends 1022, 1024 such that it follows a three dimensional path corresponding to the channel 1006. A third bend 1026 near the second end 1028 of the light conduit 1020 causes the light emitted from the second end 1028 to be directed inwardly and downwardly. By recessing the light conduit 1020 in the channel 1006 the light conduit blocks less of the passage through the cannula 1000. The second end 1028 of the light conduit may have any suitable geometry, including but not limited to those of FIGS. 1-18. A tab 1030 projects outwardly from the bracket 1032 and overhangs the flange 1004 to aid in grasping and manipulating the conduit 1020.

FIGS. 27-30 illustrate a cannula 1100 and light conduit 1150 similar to those of FIGS. 19-22. However, the light conduit 1150 is divided into multiple spaced apart conduits 1151 so that light is transmitted from a first end 1152 to second and third ends 1154, 1156 for emitting light into the cannula 1100. While the illustrative light conduit 1150 is divided into two conduits 1151 with a pair of light emitting ends 1154, 1156, it may have any number of conduits and light emitting ends. The plurality of conduits 1151 allows the individual conduits 1151 to be smaller so that they have a lower profile while the individual conduits 1151 together transmit a large amount of light to the cannula. The light emitting ends 1154, 1156 may project light along parallel paths (as shown) or they may be angled relative to one another to direct light in different directions. For example the ends 1154, 1156 may direct light to a single spot or to different locations within the surgical cavity. The light emitting ends 1154, 1156 may have any suitable geometry, including but not limited to those of FIGS. 1-18. The ends 1154, 1156 may have the same end configuration or they may have different end configurations. In the illustrative light conduit 1150 of FIGS. 27-30, the second end 1154 is convex to produce a focused beam of light and the third end 1156 is flat to produce a more dispersed beam of light. The cannula 1100 may optionally include channels (not shown) for receiving the individual spaced apart conduits 1151 to further reduce the intrusion of the conduits 1151 into the cannula 1100 interior. As with the light conduits of FIGS. 19-26, the individual light conduits of FIGS. 27-30 include first and second bends 1158, 1160 such that they each follow a three dimensional path similar to the light conduits of FIGS. 19-26. The conduit 1150 includes a tab 1170 for grasping and manipulating the conduit 1150.

Figure 32:
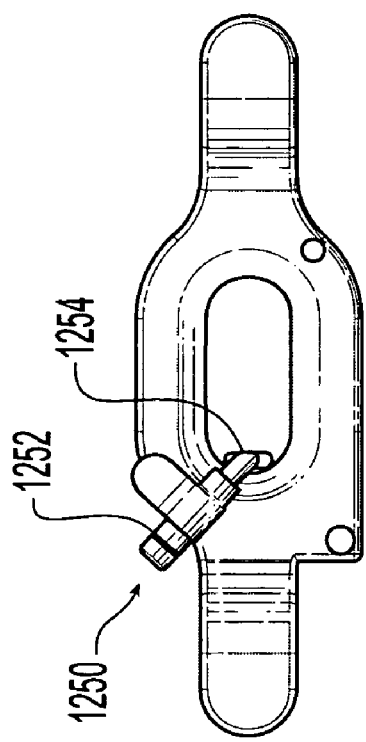
FIG. 32 shows a top plan view of the retractor of FIG. 31.
Figure 33:
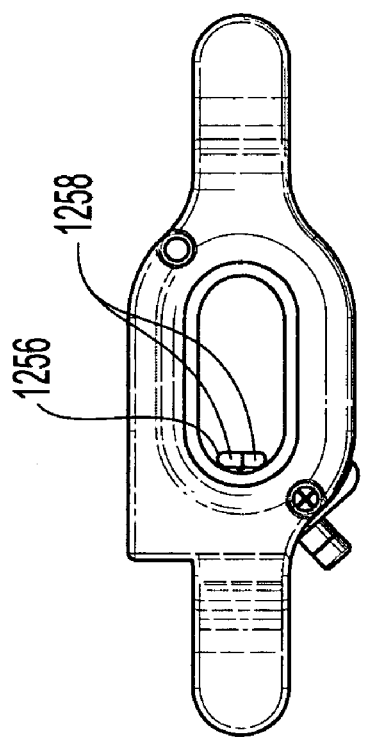
FIG. 33 shows a bottom plan view of the retractor of FIG. 31.
Figure 31:
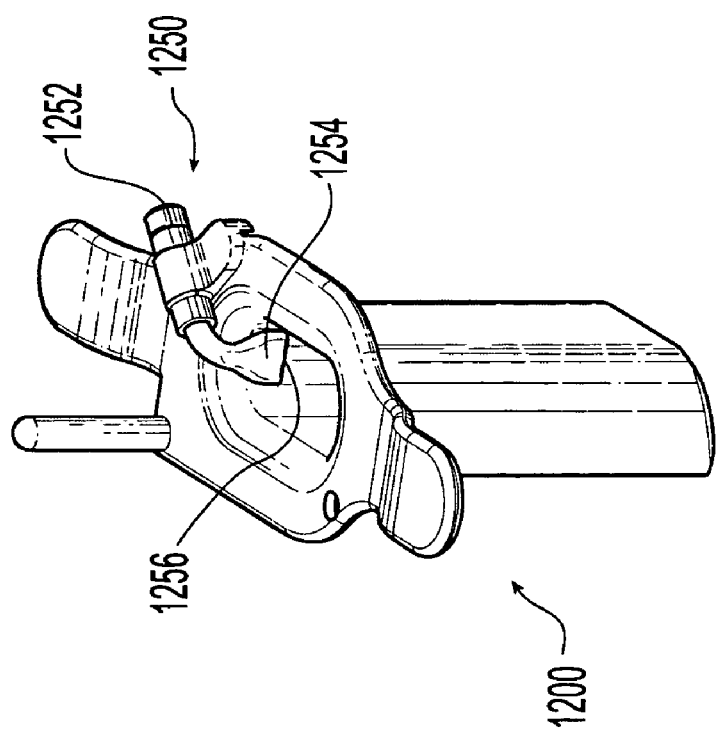
FIG. 31 shows a perspective view of an illustrative lit retractor in the form of a cannula.

FIGS. 31-33 illustrate a cannula 1200 and light conduit 1250 similar to those of FIGS. 19-22. However, the light conduit 1250 transitions from a first, generally cylindrical cross sectional region 1252 to a second, generally flattened cross sectional region 1254. Light is transmitted from the cylindrical region 1252 to the flattened region 1254. The flattened region 1254 provides a lower profile that intrudes into the interior of the cannula 1200 less than would a cylindrical region of the same cross sectional area. Such a light conduit 1250 may be made by a variety of means including molding a unitary glass or plastic conduit into the desired shape or positioning a plurality of filaments in the desired shape and adhering them together and/or encasing them in a sheath. The flattened region 1254 terminates at a light emitting end 1256. The light emitting end 1256 may have any suitable geometry, including but not limited to those of FIGS. 1-18. The illustrative light conduit 1250 of FIGS. 31-33 includes a faceted end 1256 having a pair of flat facets 1258 angled relative to one another to produce two beams of light diverging from one another like that shown in FIGS. 17-18.

FIGS. 34 and 35 illustrate a cannula 1300 and a light conduit 1350. The conduit includes an inner surface 1302 defining a passage, an outer surface 1304, a longitudinal axis 1306, and a flange 1308. The flange 1308 includes a hole 1310. The light conduit 1350 includes a body 1352 able to transmit light from a first end 1354 to a second end 1356. The first end 1354 forms a connector for attaching to a light source. In the illustrative example, the first end 1354 forms a cylindrical connector. The light conduit body 1352 adjacent to the second end 1356 is sheet-like and conforms to the inner surface 1302 of the cannula 1300. The light conduit body 1352 may be a unitary plastic or glass construction or it may be composed of a plurality of filaments. Preferably, the light conduit body 1352 includes a flexible light transmitting fabric made up of a plurality of light transmitting filaments bonded together in one or more layers. A retaining clip 1370 is engageable with the cannula 1300 to hold the light conduit 1350 in place. The retaining clip 1370 includes a body 1372 having a generally flat surface positionable opposite the flange 1308 of the cannula 1300. The body 1372 includes a peg 1374 projecting away from its flat surface and engageable with the hole 1310 in the flange 1308 to couple the retaining clip 1370 to the cannula 1300. A leg 1376 projects radially inwardly from the clip body 1372 toward the cannula axis 1306 and then bends downwardly in the longitudinal direction such that the leg 1376 is generally "L"-shaped and generally conforms to the flange 1308 and inner surface 1302 of the cannula 1300. The leg 1376 terminates in a generally arcuate foot 1378 that generally conforms to the curvature of the inner surface 1302 of the cannula 1300. The light conduit 1350 is assembled to the cannula 1300 by placing the light conduit 1350 over the flange 1308 and along the inner surface 1302. The retaining clip 1370 is then snapped in place by pressing the peg 1374 into the hole 1310 such that the leg 1376 and foot 1378 press against the light conduit 1350 and secure it against the cannula 1300. The leg 1376 and/or foot 1378 may be initially sprung away from the cannula axis 1306 such that upon engagement of the clip 1370 with the cannula 1300, spring pressure biases the leg 1376 and/or foot 1378 against the conduit 1350. The retaining clip 1370 further includes a tab 1380 projecting outwardly and overhanging the flange 1308 to permit grasping and manipulating the clip 1370.

FIGS. 36 and 37 illustrate a cannula 1400 and light conduit 1450 similar to that of FIGS. 34 and 35. The cannula includes an inner surface 1402 defining a passage, an outer surface 1404, a longitudinal axis 1406, and a flange 1408. The flange 1408 includes a fixation hole 1410. However, in the example of FIGS. 36 and 37, the light conduit filament or filaments are enclosed in a rigid housing 1452. The housing 1452 is generally "L"-shaped and includes a flange engaging portion 1454 and an inner surface engaging portion 1456 angled relative to the flange engaging portion 1454. The light conduit 1450 transmits light from a first end 1458 adjacent the flange engaging portion 1454 to a second end 1460 adjacent the inner surface engaging portion 1456. The housing 1452 is positionable on the flange 1408 with the second end 1460 projecting down into the cannula 1400. The inner surface engaging portion 1456 is concave about the cannula axis 1406 to correspond to the inner surface 1402 of the cannula 1400. The housing 1452 includes a fixation peg 1462 and a tab 1464. The light conduit 1450 attaches to the cannula 1400 by inserting the peg 1462 into a hole 1410 in the flange 1408.

The foregoing description of the invention is illustrative only, and is not intended to limit the scope of the invention to the precise terms set forth. Various embodiments have been illustrated with different forms of retractors and light conduits. Particular features of a light conduit or retractor illustrated in one embodiment may be used alone or in combination with features illustrated in other embodiments. For example a configuration having multiple, separate light conduits as shown in FIGS. 27-30 may advantageously be used with the retractor of FIGS. 1-6 to provide a low profile and/or multiple lighting effects. Further variations and modifications exist within the scope and spirit of the invention as described and defined in the following claims.

What is claimed is:

1. An apparatus for illuminated retraction of a surgical cavity, the apparatus comprising:
    a surgical retractor having a generally tubular body forming a cannula insertable into a surgical cavity, the cannula having an inner surface defining a passage from a first end to second end and an outer surface for abutting the margins of the surgical cavity;
    a light conduit including a light emitting end, the light emitting end being positioned adjacent to the passage to direct light into the passage; and
    a retaining clip engageable with the cannula to hold the light conduit in place;
    wherein the passage defines a longitudinal axis, the light conduit comprising a generally flexible, sheet-like body conformable to the inner wall of the cannula;
    wherein the retaining clip is releasably coupled to the cannula and comprises a leg projecting radially inwardly toward the cannula axis and bending downwardly into the passage, the leg terminating in a generally arcuate foot conforming to the inner surface of the cannula, the leg and foot pressing against the light conduit body to secure it to the cannula.

2. The apparatus of claim 1 wherein the light conduit is releasably coupled to the retractor.

3. The apparatus of claim 1 wherein the cannula defines an opening from the outer surface to the inner surface between the first and second ends, a portion of the light conduit lying along the outer surface of the cannula and the light emitting end being disposed within the opening.

4. The apparatus of claim 3 wherein the light emitting end projects through the opening into the passage.

5. The apparatus of claim 3 wherein the light emitting end has a shape generally corresponding to the shape of the inner surface such that it is generally flush with the inner surface.

6. The apparatus of claim 5 wherein the light emitting end has a generally curved shape.

7. The apparatus of claim 5 wherein the light emitting end has a generally planar shape.

8. The apparatus of claim 5 wherein the conduit comprises a plurality of light transmitting filaments, the filaments terminating at the light emitting end in a stair-step arrangement corresponding approximately to the shape of the inner surface of the cannula.

9. The apparatus of claim 5 wherein the conduit comprises a single light transmitting filament, the filament terminating at the light emitting end in a plurality of steps corresponding approximately to the shape of the inner surface of the cannula.

10. The apparatus of claim 5 wherein the light emitting end includes a longitudinal axis and the conduit comprises a bundle containing a plurality of filaments, the bundle terminating at the light emitting end in a planar surface oblique to the longitudinal axis of the light emitting end, each filament having an oblique end face coplanar with the planar surface.

11. The apparatus of claim 5 wherein the light emitting end includes a longitudinal axis and the conduit comprises a single filament terminating at the light emitting end in a planar surface oblique to the longitudinal axis of the light emitting end.

12. The apparatus of claim 1 wherein the light emitting end is convex.

13. The apparatus of claim 1 wherein the light emitting end is concave.

14. The apparatus of claim 1 wherein the light emitting end includes an end surface comprising a plurality of light emitting facets.

15. The apparatus of claim 1 wherein the light conduit comprises a plurality of separate light conduits, each light conduit having a light emitting end.

16. The apparatus of claim 15 wherein a first light emitting end is angled relative to a second light emitting end such the light from the first and second ends is directed in different directions.

17. The apparatus of claim 15 wherein a first light emitting end is has a different shape than a second light emitting end such the light emitted from the first end is more diffuse than the light emitted from the second end.

18. The apparatus of claim 17 wherein the first light emitting end has a shape selected from the group consisting of convex, concave, and flat and the second light emitting end has a shape selected from the group consisting of convex, concave, and flat.

19. The apparatus of claim 1 wherein the light conduit comprises a plurality of direction changing bends such that the path of the light conduit is non-planar.

20. The apparatus of claim 1 wherein the cannula body includes a channel for receiving a portion of the light conduit along a portion of one of the inner and outer surfaces.

21. The apparatus of claim 20 wherein the both the channel and light conduit comprises a plurality of direction changing bends such that the path of the light conduit is non-planar.

22. The apparatus of claim 1 wherein the passage defines a longitudinal axis and wherein the cannula further comprises a flange extending radially outwardly from the body adjacent the first end and a handle extending radially outwardly from the flange, the light conduit traversing a three dimensional path that lies adjacent to the cannula and extends tangentially relative to the axis along a portion of the handle, radially relative to the axis along a portion of the flange, and longitudinally relative to the axis along a portion of the body.

23. The apparatus of claim 1 wherein the light conduit comprises a generally circular cross sectional shape at a first end of the light conduit spaced from the light emitting end and comprises a generally non-circular cross sectional shape at the light emitting end.

24. The apparatus of claim 1 wherein the light conduit body comprises a plurality of light transmitting filaments bonded together in one or more layers.

25. The apparatus of claim 1 wherein at least a portion of the light conduit body is enclosed in a rigid housing, the shape of the housing conforming to the shape of the inner surface of the conduit.

* * * * *